(12) United States Patent
Wang et al.

(10) Patent No.: US 7,609,376 B2
(45) Date of Patent: Oct. 27, 2009

(54) METHOD AND APPARATUS FOR PIXEL DISPLAY AND SERS ANALYSIS

(75) Inventors: Shih-Yuan Wang, Palo Alto, CA (US); M. Saif Islam, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 634 days.

(21) Appl. No.: 10/968,427

(22) Filed: Jan. 5, 2005

(65) Prior Publication Data

US 2006/0147148 A1    Jul. 6, 2006

(51) Int. Cl.
G01N 21/65    (2006.01)
G01J 3/44    (2006.01)

(52) U.S. Cl. ...................................... 356/301
(58) Field of Classification Search ............. 372/26
See application file for complete search history.

(56) References Cited

U.S. PATENT DOCUMENTS

| | | | |
|---|---|---|---|
| 4,525,687 A | | 6/1985 | Chemla et al. |
| 5,339,370 A | | 8/1994 | Sano et al. |
| 5,408,486 A | * | 4/1995 | Shoji ................... 372/45.01 |
| 5,608,554 A | | 3/1997 | Do et al. |
| 5,616,986 A | * | 4/1997 | Jacobsen et al. ............ 313/461 |
| 5,652,756 A | | 7/1997 | Stultz et al. |
| 5,804,919 A | * | 9/1998 | Jacobsen et al. ............ 313/506 |
| 5,835,231 A | | 11/1998 | Pipino |
| 6,058,127 A | | 5/2000 | Joannopoulos et al. |
| 6,198,211 B1 | * | 3/2001 | Jaffe et al. ................. 313/461 |
| 6,255,670 B1 | | 7/2001 | Srivastava et al. |
| 6,392,341 B2 | * | 5/2002 | Jacobsen et al. ............ 313/506 |
| 6,404,127 B2 | * | 6/2002 | Jacobsen et al. ............ 313/506 |
| 6,448,064 B1 | | 9/2002 | Vo-Dinh et al. |
| 6,535,537 B1 | | 3/2003 | Kinoshita |
| 6,608,716 B1 | | 8/2003 | Armstrong et al. |
| 6,614,161 B1 | * | 9/2003 | Jacobsen et al. ............ 313/461 |
| 6,621,836 B2 | * | 9/2003 | Karwacki ................ 372/20 |
| 6,628,366 B2 | | 9/2003 | Wu et al. |
| 6,628,690 B1 | | 9/2003 | Fish et al. |
| 6,630,356 B1 | | 10/2003 | Armstrong et al. |
| 6,680,791 B2 | | 1/2004 | Demir et al. |
| 6,683,898 B2 | * | 1/2004 | Østergaard et al. ....... 372/43.01 |
| 6,687,447 B2 | | 2/2004 | Flory et al. |

(Continued)

FOREIGN PATENT DOCUMENTS

EP    0760544    3/1997

(Continued)

OTHER PUBLICATIONS

Ito, M et al—Enhancement of Cavity-Q in a Quasi-Three Dimensional Photonic Crystal—Japan Society of Applied Physics Extended Abstracts 2003—pp. 870-871.

(Continued)

*Primary Examiner*—F. L Evans (57) ABSTRACT

Irradiation devices and methods of amplification and irradiation are disclosed for displaying pixels and Surface Enhanced Raman Spectroscopy (SERS) analysis. The devices include an optical modulator, which may be configured for operation in a variably transmissive state. An active region may be formed in an optical waveguide with the optical modulator configured substantially adjacent at least one surface of the active region.

46 Claims, 6 Drawing Sheets

U.S. PATENT DOCUMENTS

| | | | |
|---|---|---|---|
| 6,697,548 | B2 | 2/2004 | LoCascio et al. |
| 6,711,200 | B1 * | 3/2004 | Scherer et al. .............. 372/64 |
| 6,717,348 | B2 * | 4/2004 | Takahashi .................. 313/483 |
| 6,717,353 | B1 | 4/2004 | Mueller et al. |
| 6,728,019 | B2 | 4/2004 | Usami et al. |
| 6,735,234 | B1 | 5/2004 | Paschotta et al. |
| 6,803,604 | B2 * | 10/2004 | Takahashi et al. ............. 257/80 |
| 6,829,281 | B2 * | 12/2004 | Deng et al. .................. 372/96 |
| 7,045,825 | B2 * | 5/2006 | Kahen et al. ................. 257/88 |
| 7,078,856 | B2 * | 7/2006 | Fujii ......................... 313/508 |
| 7,101,061 | B2 * | 9/2006 | Nagai et al. ................ 362/294 |
| 7,122,843 | B2 * | 10/2006 | Kahen et al. ................. 257/88 |
| 7,254,155 | B1 * | 8/2007 | Deng et al. .................. 372/97 |
| 7,391,800 | B2 * | 6/2008 | Takahashi ................. 372/50.1 |
| 2002/0068018 | A1 | 6/2002 | Pepper et al. |
| 2002/0167984 | A1 | 11/2002 | Scherer |
| 2002/0186726 | A1 | 12/2002 | Ledentsov et al. |
| 2003/0001165 | A1 | 1/2003 | Taki |
| 2003/0059154 | A1 | 3/2003 | Sato |
| 2003/0059820 | A1 | 3/2003 | Vo-Dinh |
| 2003/0227001 | A1 | 12/2003 | Li et al. |
| 2004/0090665 | A1 | 5/2004 | Futami et al. |

FOREIGN PATENT DOCUMENTS

WO    WO97/48138    12/1997

OTHER PUBLICATIONS

Lees, G P et al—"980980 nm diode pumped erbium$^{3+}$/ytterbium$^{3+}$ doped Q-switched fibre laser"—Electronics Letters vol. 31 No. 21—Oct. 12, 1995.

Tsang, D Z et al—"Qswitching of Low-Threshold Buried-Heterostructure Diode Lasers at 10 GHZ"—Applied Physics Letters vol. 45 No. 3—Aug. 1, 1984—pp. 204-206.

Emory, Steven R., et al., "Near-Field Surface-Enhanced Raman Spectroscopy on Single Silver Nanoparticles," Anal. Chem., vol. 69, No. 14, Jul. 15, 1997, pp. 2631-2635.

Kneipp, Katrin, et al., "Single Molecule Detection Using Surface-Enhanced Raman Scattering (SERS)," Physical Review Letters, vol. 78, No. 9, Mar. 3, 1997, pp. 1667-1670.

Nie, Shuming, et al., "Probing Single Molecules and Single Nanoparticles by Surface-Enhanced Raman Scattering," Science, vol. 275, Feb. 21, 1997, pp. 1102-1106.

Nie, Shuming, et al., "Optical Detection of Single Molecules," Annu. Rev. Biophys. Biomol. Struct., vol. 26, 1997, pp. 567-596.

* cited by examiner

METHOD AND APPARATUS FOR PIXEL DISPLAY AND SERS ANALYSIS

FIELD OF THE INVENTION

The present invention relates to light amplifiers and, more particularly, to light amplifiers for use in display devices and chemical analysis using Surface Enhanced Raman Spectroscopy (SERS).

BACKGROUND OF THE INVENTION

In the area of display devices, flat panel devices are increasingly replacing Cathode Ray Tubes (CRTs) in many computer and television applications. Conventional flat panels, such as Liquid Crystal Displays (LCDs) and plasma displays are becoming cost effective for many applications. At present, LCDs are one of the most popular and mature technologies for low power and cost effective implementations.

Unfortunately, conventional LCDs do not have a wide viewing angle. In other words, when the viewing direction shifts away from perpendicular to the viewing screen, the light intensity and contrast perceived from the screen decreases. As a result, appearance of the image on the LCDs may change as the viewing angle changes. Recently, Photo-Luminescent LCDs (PL-LCDs) have been developed. PL-LCDs use a fluorescent screen, similar to that of CRTs, to generate color pixels. The various colors required to generate color pixels are formed by photo-luminescent compounds that generate a specific color wavelength when exposed to an excitation radiation. Conventionally, the excitation radiation may be ultraviolet light or deep blue light. An LCD panel modulates which pixels are exposed to the excitation radiation and which pixels are not exposed at any given time. The fluorescent screen eliminates much of the viewing angle problem while still allowing the use of LCD type panels to determine which pixels to excite. Various phosphors are well known for generating the red, green, and blue wavelengths needed to cover most of the visible light spectrum.

Raman Spectroscopy is a well-known spectroscopic technique for performing chemical analysis. In conventional Raman Spectroscopy, high intensity monochromatic light from a light source, such as a laser, is directed onto an analyte to be chemically analyzed. The analyte may contain a single species of molecules or mixtures of different molecules. Furthermore, Raman Spectroscopy may be performed on a number of different molecular configurations, such as organic and inorganic molecules in crystalline or amorphous states.

The majority of the incident photons of the light are elastically scattered by the analyte molecule. In other words, the scattered photons have the same frequency, and thus the same energy, as the photons that were incident on the analyte. However, a small fraction of the photons (i.e., 1 in $10^7$ photons) are inelastically scattered by the analyte molecule at a different optical frequency than the incident photons. The inelastically scattered photons are termed the "Raman effect" and may be scattered at frequencies greater than, but most are usually scattered at a frequency lower than, the frequency of the incident photons. When the incident photons collide with the molecules and give up some of their energy, the Raman scattered photons (also referred to as Raman scattered radiation) emerge with a lower energy. The lower energy Raman scattered photons are commonly referred to in Raman spectroscopy as the "Stokes radiation." A small fraction of the molecules are already in an energetically excited state and when the incident photons collide therewith, the Raman scattered photons emerge at a higher energy. The higher energy Raman scattered photons are commonly referred to in Raman spectroscopy as the "anti-Stokes radiation." The Stokes and the anti-Stokes Raman scattered photons are detected by a detector, such as a photomultiplier, resulting in a spectral graph of intensity at a corresponding frequency (i.e., proportional to energy) for the Raman scattered photons. By plotting the frequency of the inelastically scattered Raman photons against intensity, a unique Raman spectrum, which corresponds to the particular analyte molecules, is obtained. This Raman spectrum may be used to identify chemical species, among other physical properties of the analyte. While conventional Raman Spectroscopy is suitable for bulk chemical analysis, it is not effective for surface studies because the signal from the bulk Raman scattered photons overwhelms any signal from Raman scattered photons near the surface.

Due to the deficiencies with performing surface studies using conventional Raman Spectroscopy, another Raman Spectroscopy technique called Surface Enhanced Raman Spectroscopy (SERS) which is effective for performing surface studies has been developed. In SERS, a monolayer of the molecules to be analyzed is adsorbed onto a specially roughened metal surface. Typically, the metal surface is made from gold, silver, copper, lithium, sodium, or potassium. SERS has also been used employing metallic nanoparticles or nanowires for the metal surface as opposed to a roughened metallic surface. The intensity of the Raman scattered photons from a molecule adsorbed on such a metal surface is typically about $10^4$-$10^6$ greater than conventional Raman Spectroscopy and can be as high as $10^8$-$10^{14}$. Although not thoroughly understood, the selectivity of the surface Raman signal results from the presence of surface enhancement mechanisms and is mainly attributed to two primary mechanisms: electromagnetic enhancement and chemical enhancement, with the electromagnetic enhancement being the dominant mechanism. The enhanced electromagnetic field is highly dependent on the surface roughness features of the metal surface. The chemical enhancement is believed to be dependent on the altered electronic structure of the metal surface due to adsorbing the analyte. The enhanced electromagnetic field of the metallic surface, which is adjacent to the analyte, irradiates the analyte producing an enhanced Raman signal because the strength of the Raman signal is, in part, proportional to the square of the enhanced electromagnetic field. Thus, SERS may be used to study monolayers of materials adsorbed on metals.

Due to deficiencies in the conventional technology, a SERS analysis device combining a light amplifier and optical gating with a SERS analysis surface and analyte for performing SERS may generate a stronger radiation source, the intensity of which may be controlled by a modulated signal. Furthermore, a plurality of SERS analysis devices formed on a substrate may allow spatial analysis of an analyte. This spatial analysis may be combined with varying intensities at the various SERS analysis devices. In addition, a system incorporating a light amplifier and optical gating may be combined with photo-luminescent compounds to advantageously reduce power, reduce intensity of excitation radiation, and simplify system component design for display systems.

BRIEF SUMMARY OF THE INVENTION

The present invention, in a number of embodiments, includes irradiation devices and methods of amplification and irradiation. The devices and methods may be used for displaying pixels and Surface Enhanced Raman Spectroscopy (SERS) analysis.

In one embodiment of the present invention, an irradiation device includes an optical modulator, which may be configured for operation in a variably transmissive state. An active region may be formed in an optical waveguide with the optical modulator configured such that it is substantially adjacent at least one surface of the active region. The active region may be further configured for generating an amplified radiation derived from an incident pump radiation impinging on the optical waveguide. The amplified radiation may be generated when the variably transmissive state of the optical modulator is configured as substantially non-transmissive. The irradiation device also includes an exposure region configured to be illuminated by the amplified radiation when the optical modulator is configured in the variably transmissive state.

In another embodiment of the present invention, an irradiation array comprises an array of a plurality of the irradiation devices described above.

Another embodiment of the present invention includes a Surface Enhance Raman Spectroscopy System (SERS), comprising an irradiation device as described above and a SERS-active structure disposed within the exposure region and configured to accept an analyte thereon. The SERS-active structure and the analyte are configured to emit a Raman scattered radiation when exposed to the amplified radiation from the irradiation device.

Another embodiment of the present invention includes a method for amplification and irradiation comprising illuminating an optical waveguide, including an active region formed therein, with an incident pump radiation. The amplified radiation may be generated in the active region using the incident pump radiation by configuring an optical modulator, disposed substantially adjacent at least one surface of the active region, in a substantially non-transmissive state. The amplified radiation may be variably discharged through the optical modulator to illuminate an exposure region by configuring the optical modulator in a variably transmissive state.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

In the detailed description, various references may be made using directional indicators such as top, bottom, side, up, and down. These directional indicators are used to assist in describing the various structures of the present invention and do not imply that the present invention must be oriented as described unless otherwise noted.

The present invention, in a number of embodiments, includes structures and irradiation devices for generating an amplified radiation, which may be useful in applications such as display devices and systems for Surface Enhanced Raman Spectroscopy (SERS) analysis.

Figure 1:
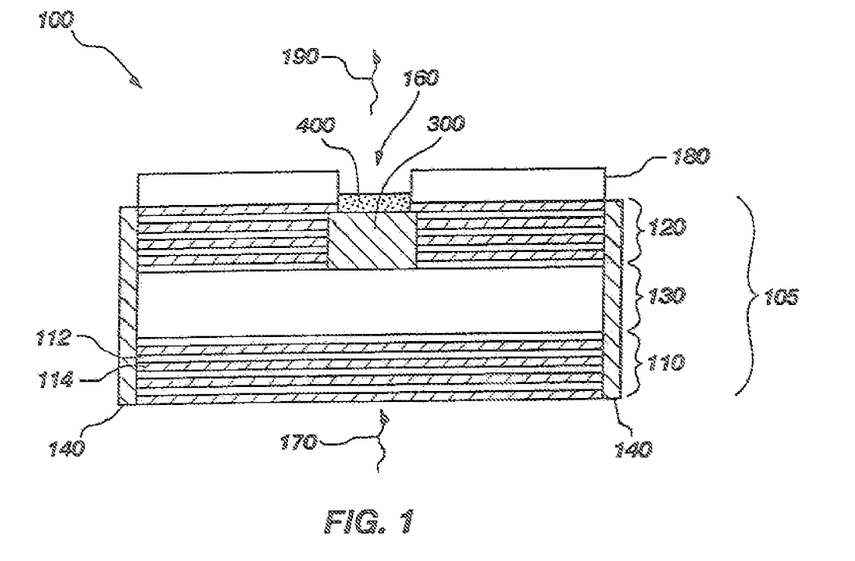
FIG. 1 is a cross section view of an exemplary optically pumped irradiation device with an optical modulator disposed above an active region of an optical waveguide.

FIG. 1 illustrates an exemplary irradiation device 100 including an optical waveguide 105, an optical modulator 300, an exposure region 160 for receiving amplified radiation from the optical waveguide 105, and a medium of interest 400 for exposure to the amplified radiation. When the present invention is practiced as a display device, the medium of interest 400 may be various photo-luminescent compounds (shown in FIGS. 10A and 10B). When the present invention is practiced as a SERS analysis device, the medium of interest 400 may be a SERS-active structure 420 (shown in FIG. 11) with an analyte 430 for analysis disposed on the SERS-active structure 420.

The optical waveguide 105 in FIG. 1 is formed by a first Bragg reflector 110 and a second Bragg reflector 120 oriented in a substantially parallel plane to the first Bragg reflector 110 and separated by an active region 130. To enhance amplification, the active region 130 may include one or more quantum wells.

Bragg reflectors (also referred to as Bragg Mirrors) are one-dimensional photonic crystals. A one-dimensional photonic crystal is a three-dimensional structure that exhibits periodicity in refractive index in only one dimension. Alternating layers of low and high refractive index material create this periodicity in the direction orthogonal to the planes of the alternating layers. Periodicity is not exhibited in either of the two orthogonal dimensions contained within the plane of the films.

Photonic crystals, such as Bragg reflectors, may exhibit a photonic bandgap within a range of certain frequencies in the directions exhibiting periodicity in refractive index. In other words, there is a range of frequencies of radiation or light that will not be transmitted through the crystal in the directions exhibiting periodicity in refractive index. This range of frequencies that are not transmitted is known as the photonic bandgap of the photonic crystal.

Bragg reflectors may be formed in a number of ways using a variety of materials configured as alternating layers of low and high refractive index. Each layer is configured with a thickness of about a quarter wavelength of the light to be amplified by the irradiation device 100. Due to this quarter-wave thickness, the resulting Bragg reflector may also be referred to as a quarter-wave stack. As an example, a Bragg reflector may be formed from alternating layers of GaAs (gallium arsenide) and AlGaAs (aluminum gallium arsenide). Another suitable material combination for forming Bragg reflectors is alternating layers formed respectively from silicon and silicon dioxide.

In FIG. 1, Bragg reflectors 110 and 120 may be formed from alternating first layers 112 and second layers 114. Generally, more layers create a higher reflectivity index. The second Bragg reflector 120 may include more layers resulting in a higher reflectivity index, thus increasing the possible optical gain within the optical waveguide 105. On the other hand, the first Bragg reflector 110 may include fewer layers, reducing the optical gain somewhat but allowing more incident pump radiation 170 to penetrate through the first Bragg reflector 110 and into the active region 130 where the incident pump radiation 170 can be amplified.

Edge reflectors 140 may be formed at the lateral edges of the active region 130. These edge reflectors 140 may be formed to be substantially reflective to the wavelength of the incident pump radiation 170. The substantial reflectivity may be obtained using structures such as Distributed Bragg Reflectors (DBR). Alternatively, in the case where the irradiation device 100 is formed as an individual device intended to be separated from a substrate, the edge reflectors 140 may be formed by cleaving the lateral edges of the irradiation device 100, similar to the process for forming a laser diode. Due to the reflective property, the edge reflectors 140 in combination with the first Bragg reflector 110 and second Bragg reflector 120 form a Fabry-Perot cavity (also referred to as an optical waveguide 105) to contain and amplify the incident pump radiation 170.

If desired, the irradiation device 100 may be fabricated on a support substrate (not shown), such as, for example, a silicon substrate, a GaAs substrate, or a glass substrate. After fabrication, the support substrate may be removed if desired. On the other hand, if the support substrate is optically transparent to the incident pump radiation 170, the support substrate need not be removed.

The optical modulator 300 may be disposed in either the first Bragg reflector 110 or the second Bragg reflector 120. FIG. 1 illustrates the optical modulator 300 placed in the second Bragg reflector 120. An exposure region 160 may be formed above the optical modulator 300. The exposure region 160 may be formed within the first Bragg reflector 110. Alternatively, a confinement layer 180 may be formed on the first Bragg reflector 110 with a cavity in the confinement layer 180 to form the exposure region 160. In addition, the exposure region 160 may be formed partially in the first Bragg reflector 110 and partially in the confinement layer 180. The confinement layer 180 may be formed of any suitable material, such as, for example a passivation layer, silicon dioxide, photo-curable resin, or thermal-curable resin.

The optical modulator 300, when enabled, may variably transmit light in a direction from the active region 130 to the exposure region 160, generating an excitation radiation 190. Detailed operation of the optical modulator 300 is explained more fully below.

Figure 2:
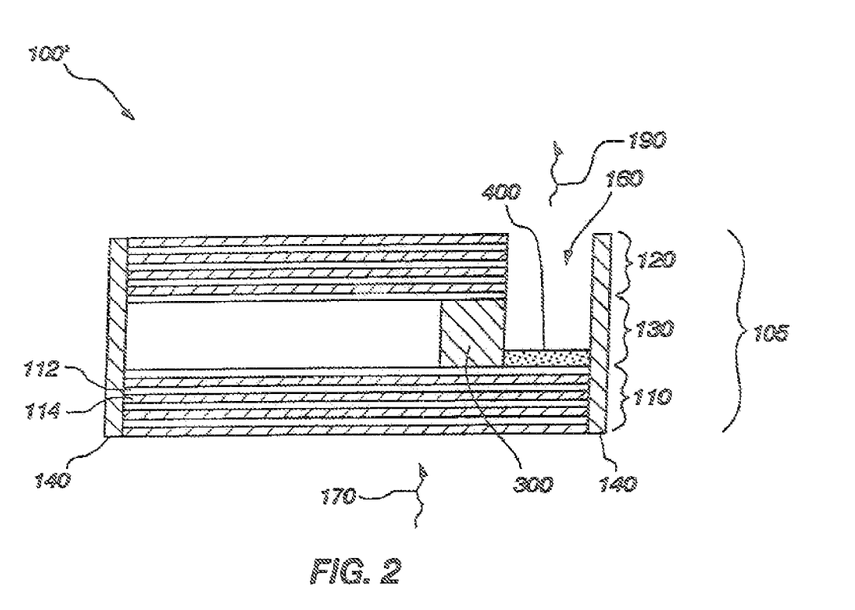
FIG. 2 is a cross section view of another exemplary optically pumped irradiation device with the optical modulator disposed within the active region of the optical waveguide.

FIG. 2 illustrates another embodiment of the irradiation device 100' similar to the irradiation device 100 of FIG. 1. However, in the FIG. 2 embodiment, the optical modulator 300 is disposed in the active region 130 between the first Bragg reflector 110 and the second Bragg reflector 120. Additionally, the exposure region 160 is shown disposed laterally adjacent the optical modulator 300 such that the amplified radiation may be variably transmitted through the optical modulator 300 from the active region 130 to the exposure region 160. The exposure region 160 may extend through at least a portion of the active region 130 and the first Bragg reflector 110. The medium of interest 400 may be disposed within the exposure region 160. As with the FIG. 1 embodiment, the exposure region 160 may be formed through the first Bragg reflector 110 or the second Bragg reflector 120, depending on the desired orientation.

Figure 3:
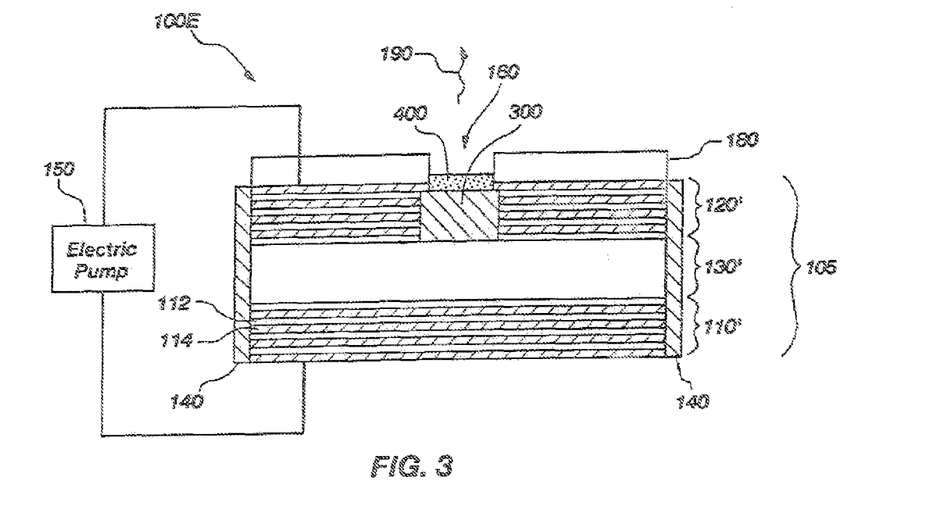
FIG. 3 is a cross section view of an exemplary electrically pumped irradiation device with an optical modulator disposed above an active region of an optical waveguide.

FIG. 3 illustrates an embodiment of an irradiation device 100E similar to the FIG. 1 embodiment of the irradiation device 100. However, in the FIG. 3 embodiment, the first Bragg reflector 110' is a P-doped material and the second Bragg reflector 120' is an N-doped material. When configured with an electrical pump 150, rather than an optical pump, these doped materials along with an appropriate active region 130' may be configured to generate a desired wavelength of light, similar to an edge emitting laser diode. It will be readily apparent to a person of ordinary skill in the art that the doping and polarity of the electrical pump may be reversed, such that the first Bragg reflector 110' is an N-doped material and the second Bragg reflector 120' is a P-doped material.

As with the FIG. 1 embodiment, the optical modulator 300 in the FIG. 3 embodiment may be disposed in either the first Bragg reflector 110 or the second Bragg reflector 120. FIG. 3 illustrates the optical modulator 300 placed in the second Bragg reflector 120. In addition, an exposure region 160 may be formed above the optical modulator 300.

Figure 4:
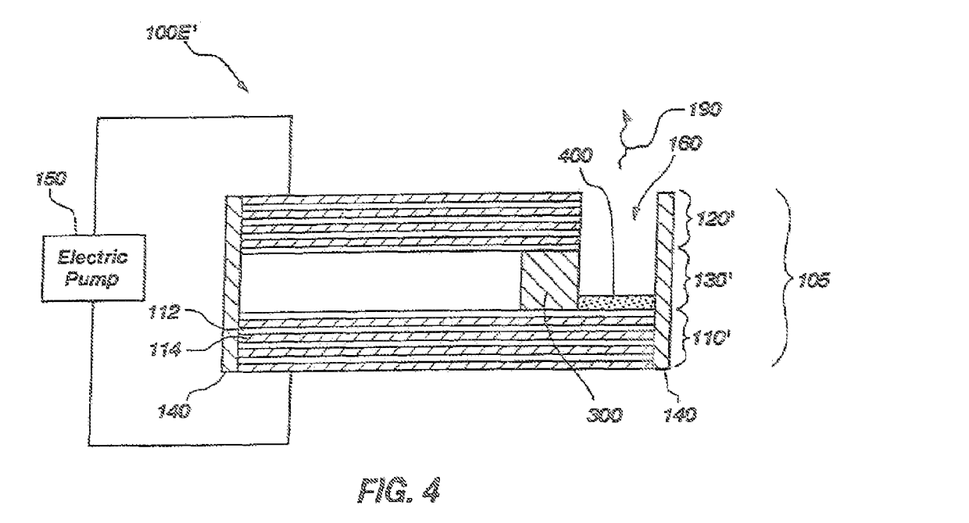
FIG. 4 is a cross section view of another exemplary electrically pumped irradiation device with the optical modulator disposed within the active region of the optical waveguide.

FIG. 4 illustrates an embodiment of an irradiation device 100E' similar to the FIG. 2 embodiment of the irradiation device 100' However, in the FIG. 4 embodiment, the first Bragg reflector 110' is a P-doped material and the second Bragg reflector 120' is an N-doped material. When configured with an electrical pump 150, rather than an optical pump, these doped materials along with an appropriate active region 130' may be configured to generate a desired wavelength of light, similar to an edge emitting laser diode. It will be readily apparent to a person of ordinary skill in the art that the doping and polarity of the electrical pump may be reversed, such that the first Bragg reflector 110' is an N-doped material and the second Bragg reflector 120' is a P-doped material.

As with the FIG. 2 embodiment, the optical modulator 300 may be disposed in the active region 130 between the first Bragg reflector 110 and the second Bragg reflector 120. Additionally, the exposure region 160 is shown disposed laterally adjacent the optical modulator 300 such that the amplified radiation may be variably transmitted through the optical modulator 300 from the active region 130 to the exposure region 160.

Figure 5:
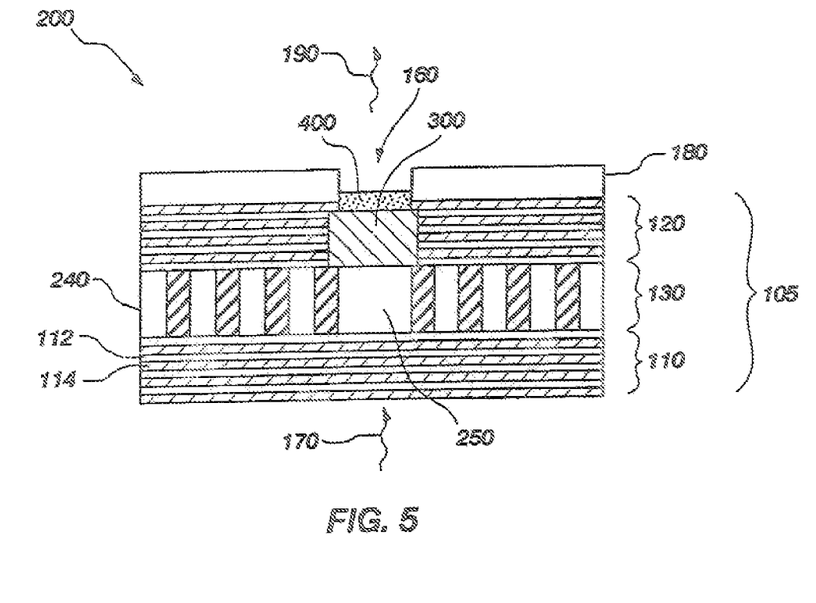
FIG. 5 is a cross section view of an exemplary optically pumped irradiation device with an optical modulator disposed above a photonic crystal material of an optical waveguide.
Figure 7A:
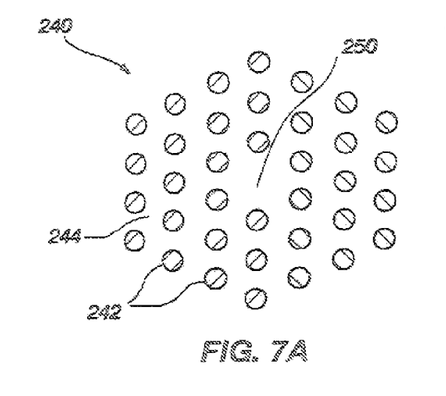
FIG. 7A is a top view of an exemplary two-dimensional photonic crystal.
Figure 7B:
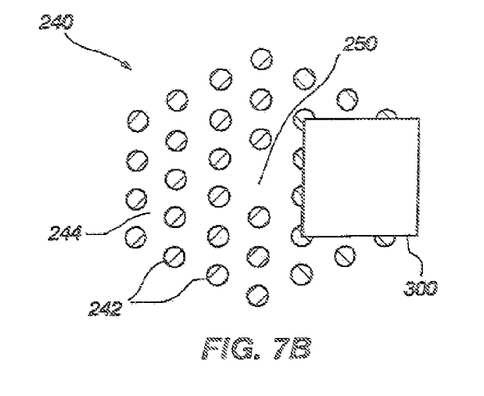
FIG. 7B is a top view of an exemplary two-dimensional photonic crystal and an exemplary placement of an optical modulator.

FIG. 5 illustrates another embodiment of the irradiation device 200 capable of achieving even higher radiation amplification than the previous embodiments. In the FIG. 3 embodiment, rather than containing quantum wells, the active region contains a two-dimensional photonic crystal material 240 (as shown in FIGS. 7A and 7B). A two-dimensional photonic crystal material 240 may be formed by periodically dispersing rods or columns 242 of a material of one refractive index within a matrix 244 having a different refractive index. Two-dimensional photonic crystals exhibit periodicity in only two dimensions (i.e., the directions perpendicular to the length of the rods or columns 242), but no periodicity is exhibited in the direction parallel to the length of the columns 242. The periodicity of the two-dimensional photonic crystal material 240 and the Bragg reflectors is chosen to reflect the wavelength of the incident pump radiation 170.

The photonic crystal material 240, as shown in a top view in FIGS. 7A and 7B, creates a highly refractive behavior in the two dimensions of the photonic crystal material 240 periodicity. A defect 250 may be created in the photonic crystal material 240. The defect 250 may be formed by removing or failing to form one column near the center of the cavity layer. Alternatively, the defect 250 may be formed as an air gap or a spatially confined area of a different material such as glass or epoxy. The defect 250 in the photonic crystal material 240 creates a high-Q cavity 250 at the sight of the defect 250 due to the high reflectivity in the plane perpendicular to the columns 242. The high-Q cavity 250 is completed by the high reflectivity of the first Bragg reflector 110 and second Bragg reflector 120 on either side of the two-dimensional photonic crystal material 240. The resulting high-Q cavity 250 may exhibit an enhanced amplification over the quantum well active region 130 because of the small confinement region and because the amplified light within the high-Q cavity 250 cannot propagate laterally to escape therefrom.

Figure 6:
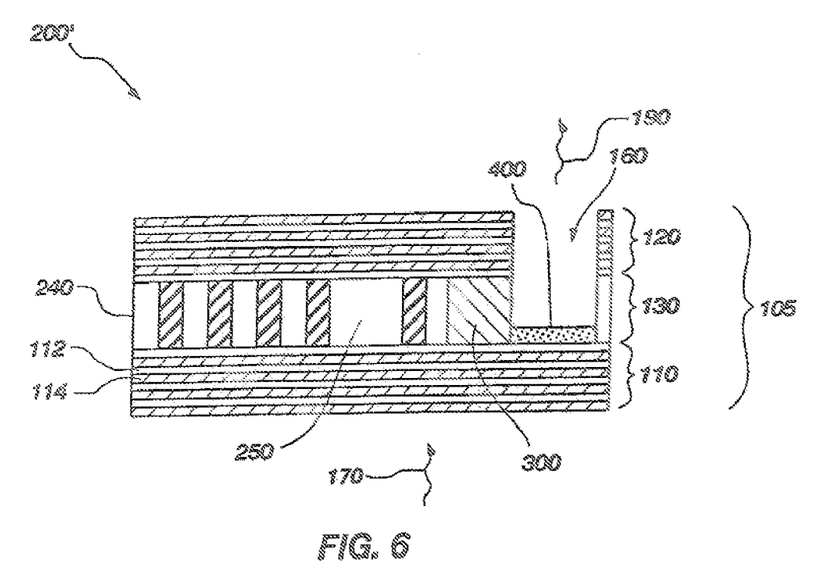
FIG. 6 is a cross section view of another exemplary optically pumped irradiation device with the optical modulator disposed within the photonic crystal material of the optical waveguide.

FIG. 6 illustrates another embodiment of the irradiation device 200' similar to the irradiation device 200 of FIG. 5. However, in the FIG. 6 embodiment, the optical modulator 300 is disposed in the photonic crystal material 240 substantially near the high-Q cavity 250 and between the first Bragg reflector 110 and the second Bragg reflector 120 (as shown in FIG. 6 and FIG. 7B). Additionally, the exposure region 160 is shown disposed laterally adjacent the optical modulator 300 such that the amplified radiation may be variably transmitted through the optical modulator 300 from the high-Q cavity 250 to the exposure region 160. The exposure region 160 may extend through at least a portion of the two-dimensional photonic crystal material 240 and the first Bragg reflector 110. The medium of interest 400 may be disposed within the exposure region 160. As with the FIG. 1 embodiment, the exposure region 160 may be formed in the first Bragg reflector 110 or the second Bragg reflector 120, depending on the desired orientation.

Figure 8A:
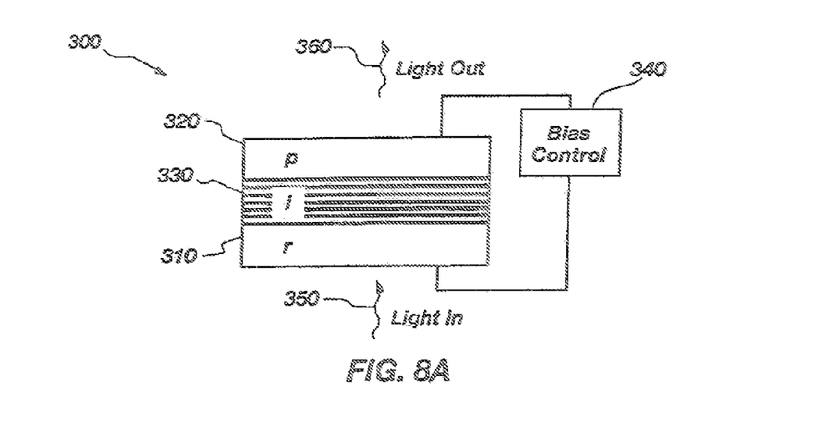
FIG. 8A is a cross section view of an exemplary optical modulator.
Figure 8B:
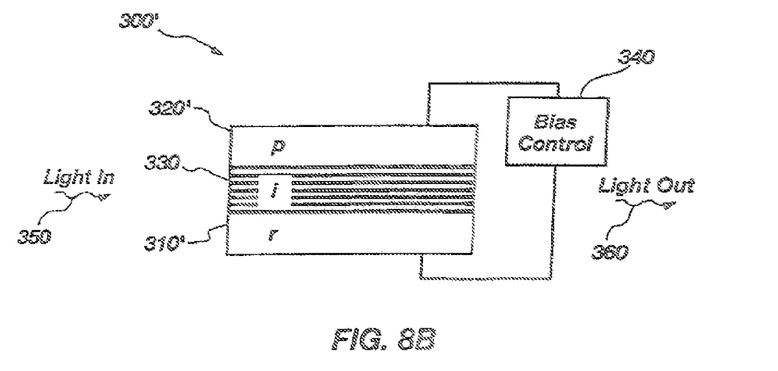
FIG. 8B is a cross section view of another exemplary optical modulator.

Exemplary implementations of optical modulators 300 are shown in FIGS. 8A and 8B. Generally, an optical modulator 300 may be configured as a quantum well diode. The diode may be formed as an intrinsic layer 330 sandwiched between a p-type layer 320 and an n-type layer 310. Conventionally, the resulting diode is often referred to as a PIN diode because of the sandwich structure of a p-type layer 320, an intrinsic layer 330, and an n-type layer 310. A bias control 340 may apply an electrical field between the p-type layer 320 and the n-type layer 310.

In an optical modulator 300, the intrinsic layer 330 may be composed of a material, such as, for example, InGaAsP for a bulk material, or InGaAs/InGAIAs for a multiple quantum well structure. The intrinsic layer 330 may have an electric field dependent absorption coefficient or an electric field dependent refractive index. In bulk intrinsic layers 330, the absorption effect is often referred to as the Franz-Keldysh effect, while in quantum well intrinsic layers 330, the absorption effect is often referred to as the Stark effect. The refractive index associated with any change in the absorption spectrum of a material is very closely related to the absorption coefficient. This association is often referred to as a Kramer-Kronig relation.

By reverse biasing the optical modulator 300 (i.e., the PIN diode), the absorption coefficient of the intrinsic layer 330 may be modified. The amount of energy in the electrical field varies the absorption coefficient such that the intrinsic layer 330 may have a variably transmissive state from substantially non-transmissive to substantially transmissive.

In operation, as shown in FIG. 8A, an input beam 350 impinges on an external surface of the n-type layer 310 and is substantially transmitted to the intrinsic layer 330. Depending on the electrical field applied to the intrinsic layer 330 by the bias control 340, the intrinsic layer 330 transmits a variable portion of the input beam 350 through the p-type layer 320 to an output beam 360. Of course, the light direction may easily be configured in the opposite direction such that the input beam 350 impinges on the p-type layer 320 and the output beam 360 emanates from the n-type layer 310.

FIG. 8B shows another embodiment of an optical modulator 300'. In this embodiment, the p-type layer 320 and n-type layer 310 may be formed as Bragg reflectors, similar to those described above by doping the materials making up the Bragg reflectors with a p-type dopant and an n-type dopant, respectively. The Bragg reflectors form an optical waveguide through the intrinsic layer 330. An input beam 350 directed at a plane substantially parallel to the plane of the PIN diode structure may enter the intrinsic layer 330. Depending on the electrical field applied to the intrinsic layer 330 by the bias control 340, the intrinsic layer 330 transmits a variable portion of the input beam 350 to an output beam 360 emanating from the opposite end of the intrinsic layer 330.

Operation of the various irradiation devices (100, 100', 200 and 200') is described in reference to FIGS. 1-4 illustrating embodiments of the irradiation device (100, 100', 200 and 200') and FIGS. 8A and 8B illustrating embodiments of the optical modulator (300 and 300'). In reference to FIGS. 1 and 2, incident pump radiation 170 is directed at the first Bragg reflector 110. The incident pump radiation 170 may be of a relatively low intensity, which may result in reduced power requirements, because of the amplification properties of all the embodiments of the irradiation device (100, 100', 200 and 200'). A portion of the incident pump radiation 170 is transmitted through the first Bragg reflector 110 into the active region 130. If the optical modulator 300, positioned in the second Bragg reflector 120 in FIG. 1, is configured to be substantially non-transmissive, the Fabry-Perot cavity formed in the active region 130 may amplify the radiation in the active region 130 because very little light can escape due to the reflective properties of the material comprising the Fabry-Perot cavity. With the radiation amplified, the optical modulator 300 may be configured in a variably transmissive state, allowing some of the amplified radiation in the active region 130 to be transmitted to the exposure region 160. The radiation transmitted through the optical modulator 300 is referred to as excitation radiation 190. The excitation radiation 190, impinges on the medium of interest 400 to create various effects depending on the medium of interest 400, as is explained more fully below.

Either embodiment of the optical modulator (300 or 300') may be used in the irradiation device 100 embodiment of FIG. 1. However, because the radiation travels in a direction perpendicular to the layers of the Bragg reflectors, it may be easier to implement the optical modulator 300 embodiment of FIG. 8A. If the FIG. 8A embodiment is used, the layers forming the PIN diode lie in the same plane as the layers of the first and second Bragg reflectors 110 and 120, which may make fabrication easier.

In reference to FIG. 2, operation of the irradiation device 100' is similar to that of the FIG. 1 embodiment. However, in the FIG. 2 embodiment, the optical modulator 300 is disposed in the active region 130. As a result, the amplified radiation that may be transmitted from the active region 130 through the optical modulator 300 to the exposure region 160 is transmitted in a direction parallel to the plane of the first and second Bragg reflectors 120. As with the FIG. 1 embodiment, either embodiment of the optical modulator (300 or 300') may be used in the irradiation device 100 of FIG. 2. However, because the radiation travels in a direction parallel to the layers of the Bragg reflectors, it may be easier to implement the optical modulator 300' embodiment of FIG. 8B. If the FIG. 8B embodiment is used, the layers forming the PIN diode lie in the same plane as the layers of the first and second Bragg reflectors 120, which may make fabrication easier.

In reference to FIGS. 5 and 6, operation of the irradiation device 200 and 200' is similar to that of the FIGS. 1 and 2. Particularly, the operation of the optical modulator (300 or 300') and transmission of amplified radiation to the exposure region 160 is the same. However, amplification of the radiation is somewhat different for the FIGS. 5 and 6 embodiments due to the two-dimensional photonic crystal material 240. Incident pump radiation 170 is directed at the first Bragg reflector 110. Because of the increased amplification properties of the two-dimensional photonic crystal material 240 embodiments of the irradiation device (200 and 200'), the incident pump radiation 170 may be of an even lower intensity than the active region 130 embodiments of FIGS. 1 and 2. A portion of the incident pump radiation 170 is transmitted through the first Bragg reflector 110 into the two-dimensional photonic crystal material 240. If the optical modulator 300, positioned in the second Bragg reflector 120 in FIG. 5, is configured in a substantially non-transmissive state, the high-Q cavity 250 formed by the defect 250 in the two-dimensional photonic crystal material 240 may amplify the radiation. The amplification in the high-Q cavity 250 may occur because very little light can escape due to the reflective properties of the material comprising the high-Q cavity 250 and the adjacent optical modulator 300. With the radiation amplified, the optical modulator 300 may be configured in a variably transmissive state, allowing some of the amplified radiation in the high-Q cavity 250 to be transmitted to the exposure region 160.

As with the FIGS. 1 and 2 embodiments, the embodiment of optical modulator 300 used may depend on the location of the optical modulator 300. In other words, it may be easier to implement the FIG. 8A embodiment of the optical modulator 300 in an irradiation device 200 with the optical modulator 300 positioned in one of the Bragg reflectors. On the other hand, it may be easier to implement the FIG. 8B embodiment of the optical modulator 300' in an irradiation device 200' with the optical modulator 300' positioned in the two-dimensional photonic crystal material 240.

The excitation radiation 190 entering the exposure region 160 impinges on the medium of interest 400. If the irradiation device (100, 100', 200 and 200') is to be configured for SERS evaluation, the medium of interest 400 may be a SERS-active structure 420 and an analyte 430 (shown in FIG. 11). If the irradiation device (100, 100', 200 and 200') is to be configured as a display device, the medium of interest 400 may be a photo-luminescent compound 410 (shown in FIGS. 10A and 10B).

Figure 10A:
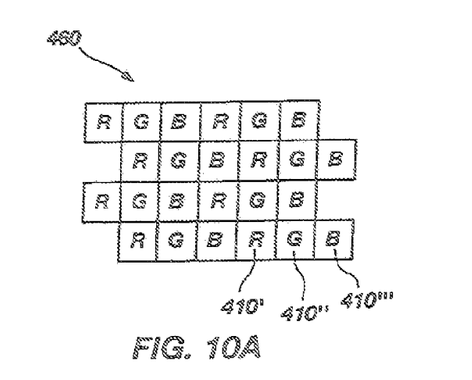
FIGS. 10A and 10B show exemplary layouts of various photo-luminescent compounds that may be used in forming a color pixel for a display device.
Figure 10B:
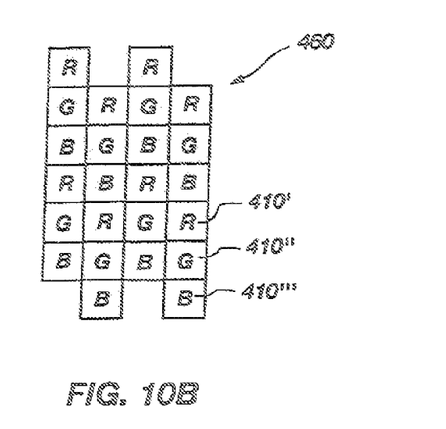

Various photo-luminescent compounds 410 may be used to generate different colors of a selected light wavelength. Various phosphors are well known that may be excited by excitation radiation 190 in both the ultraviolet and deep-blue radiation spectrums. These well known phosphors may be selected to emit light in the selected light wavelengths of substantially red, substantially green and substantially blue. A display pixel 460 may include only one type of phosphor to create a monochromatic pixel. Alternatively, a display pixel 460 may include three irradiation devices (such as, e.g., 100, 100', 200 and 200') configured as one pixel 460 with a substantially red emitting phosphor 410', one device with a substantially green emitting phosphor 410", and one device with a substantially blue emitting phosphor 410'''. The resulting display pixel 460 may be capable of generating substantially near the full visible light spectrum.

Figure 11:
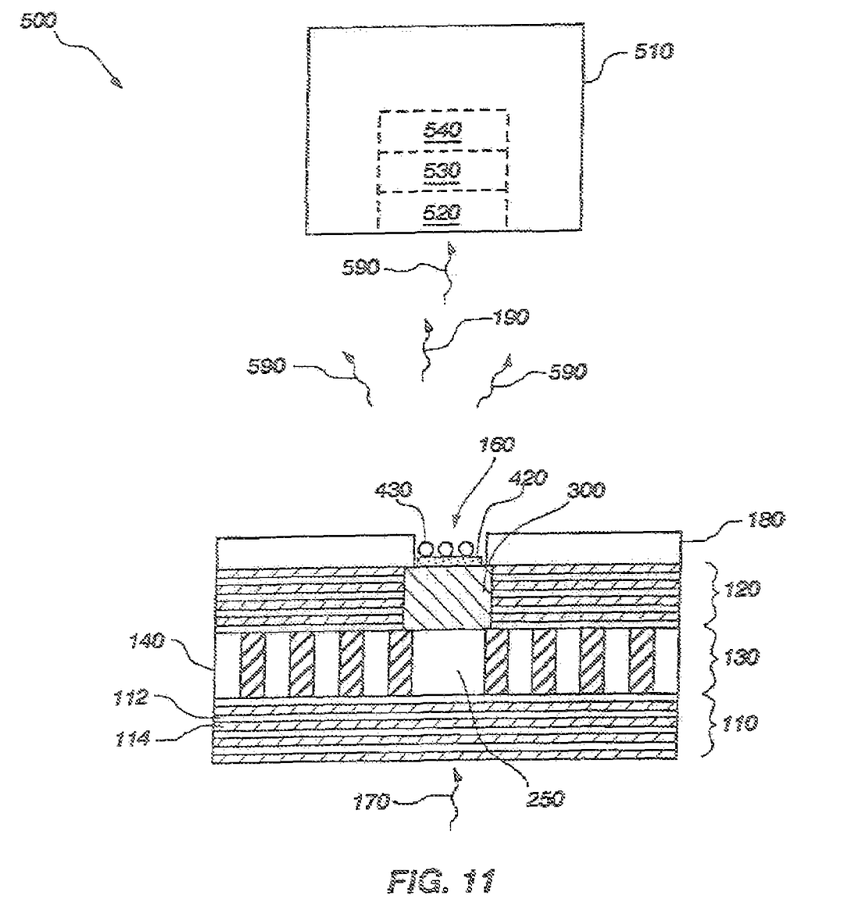
FIG. 11 shows a SERS system including the irradiation device, a SERS-active structure, an analyte, and a SERS sampling device.

As shown in FIG. 11, the structures and devices of the present invention may incorporate a SERS-active structure 420 as the medium of interest 400 disposed within the exposure region 160 of the irradiation device 200. The SERS-active structure 420 may be used to effect the electromagnetic enhancement of the Raman signal, chemical enhancement of the Raman signal, or both. As used herein, the term "SERS-active structure" means any structure configured and formed of a material that may produce chemical enhancement of the Raman signal, electromagnetic enhancement of the Raman signal, or both. Exemplary materials for the SERS-active structure 420 include gold, silver, copper, aluminum, chromium, lithium, sodium, potassium, or another suitable material that may produce chemical enhancement of the Raman signal, electromagnetic enhancement of the Raman signal, or both.

The SERS-active structure 420 enhances Raman scattered radiation 590 generated when the excitation radiation 190 irradiates the SERS-active structure 420 and an analyte 430 disposed on the SERS-active structure 420.

It has been shown that a relatively rough surface enhances the amount of Raman scattered radiation 590 that may emanate from the SERS-active structure 420 when an analyte 430 disposed on the SERS-active structure 420 is irradiated. As a result, the SERS-active structure 420 may be formed as a single monolithic layer, possibly with a roughened surface, or the SERS-active structure 420 may comprise one or more discrete particles.

As a layer, the SERS-active structure 420 may be disposed on an analysis surface of the exposure region 160. The SERS-active structure 420 may be disposed by chemically bonding or merely disposing on the analysis surface and weakly bonding thereto, if bonded at all.

As one or more discrete particles, the SERS-active structure 420 may have a variety of exemplary configurations such as, nanowires (i.e., a rod shaped configuration), nanodots, nanoparticles (including employing a single nanoparticle), or metallic particles in a colloidal suspension. It is currently preferred to employ at least two silver nanoparticles spaced apart such that an analyte 430 molecule may be draped therebetween. The aforementioned nanostructures for the SERS-active structure 420 may be formed by chemical vapor deposition (CVD), molecular beam epitaxy (MBE), atomic layer deposition (ALD), or any other suitable technique to deposit the SERS-active structure 420 on the analysis surface.

Figure 9:
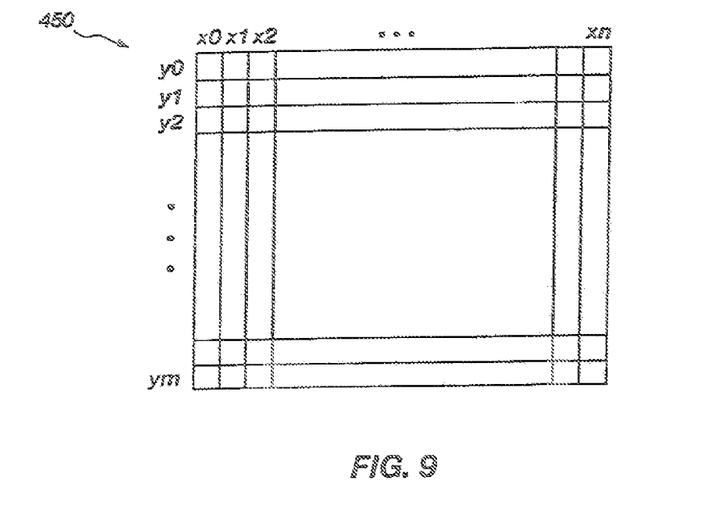
FIG. 9 show an exemplary layout of an irradiation array for a display device or SERS analysis.

FIG. 9 illustrates an exemplary irradiation array 450 of a plurality of irradiation devices (100, 100', 200 and 200'), which may be formed on a substrate. FIG. 9 is exemplary of a possible rectilinear arrangement of irradiation devices (100, 100', 200 and 200') wherein the number of irradiation devices (100, 100', 200 and 200') in the x direction (i.e., x0 to xn) and number of irradiation devices 100 in the y direction (i.e., y0 to yn) may be a variety of values depending on size and application of the irradiation array 450.

When the irradiation array 450 is used as a display device, each irradiation device (100, 100', 200 and 200') may be considered a display pixel 460 and the display device may be configured as monochromatic. In other words, all the display pixels 460 may be configured to emit the same color. In a monochromatic display, the medium of interest 400 disposed in each irradiation device 100 in the irradiation array 450 may be of the same type. In other words, to create a green display, for example, the medium of interest 400 may be a photoluminescent compound 410" that emits substantially green light.

However, the irradiation array 450 may be configured as a full color display. As a full color display, each pixel 460 may be comprised of multiple irradiation devices (100, 100', 200 and 200') including different photo-luminescent compounds (410', 410", and 410''') for each irradiation device (100, 100', 200 and 200') in the pixel 460 for generation of the full visible light spectrum, as explained above.

Exemplary spatial configurations of the color pixels 460 are shown in FIGS. 10A, and 10B. FIG. 10A shows an exemplary pixel 460 arrangement where each pixel 460 is aligned horizontally. In other words, a pixel 460 is comprised of a row comprising a red photo-luminescent compound 410', a green photo-luminescent compound 410", and a blue photo-luminescent compound 410'''. Conventionally the next row of pixels 460 may have the red, green, and blue portions staggered to prevent possible formation of vertical color lines.

FIG. 10B shows an exemplary pixel 460 arrangement where each pixel 460 is aligned vertically. In other words, a pixel 460 is comprised of a column comprising a red photo-luminescent compound 410', a green photo-luminescent compound 410", and a blue photo-luminescent compound 410'''. Conventionally the next column of pixels 460 may have the red, green, and blue portions staggered to prevent possible formation of horizontal color lines.

While the pixel 460 portions of red, green, and blue are shown as square in FIGS. 10A and 10B, they may be formed in a more rectangular shape such that the overall color pixel 460 formed of the three portions is more square. Additionally, it will be readily apparent to a person of ordinary skill in the art that many other pixel 460 configurations may be contemplated as within the scope of the present invention.

In addition to a display device, the irradiation array 450 may be used for SERS analysis. The array form may assist in analyzing varying concentrations of an analyte 430 at different spatial locations within the array.

In FIG. 11, a SERS system 500 includes an irradiation device (100, 100', 200 and 200'), from any one of the embodiments described above, shown herein for illustrative purposes as device 200, wherein the medium of interest 400 disposed in the exposure region 160 is a SERS-active structure 420 with an analyte 430 disposed thereon. The SERS system 500 also includes a detector 510, which may include a lens 520 or lens assembly for collecting Raman scattered radiation 590 (i.e., photons).

The wavelengths emitted by the irradiation device (100, 100', 200 and 200') as excitation radiation 190 may be any suitable wavelength for properly analyzing the analyte 430. By way of example and not limitation, a representative range for the wavelengths that may be emitted by the light source is about 350 nm to about 1000 nm.

The irradiation of the SERS-active structure 420 and analyte 430 by excitation radiation 190 impinging on the SERS-active structure 420 and analyte 430 in part produces a strong electromagnetic field in the SERS-active structure 420. Because the electromagnetic field is adjacent to the analyte 430, the analyte 430 is, in turn, irradiated by a very strong electromagnetic field. The irradiation of the analyte 430 by the enhanced field from the SERS-active structure 420 produces the aforementioned Stokes, anti-Stokes, or Stoke and anti-Stokes, Raman scattered photons 590 (also referred to as Raman scattered radiation 590) that are characteristic of the particular analyte 430 being analyzed. Because the intensity of the Raman scattered photons 590 is, in part, proportional to the square of the electromagnetic field that irradiates the analyte 430, the enhancement effect from the SERS-active structure 420 may increase the intensity of the Raman signal by as much as $10^{14}$.

Ideally, the Raman scattered photons 590 are isotropic, being scattered in all directions. If the scattering is isotropic, the position of the detector 510 is not particularly important. However, if the wavelength of the excitation radiation 190 is close to the wavelength of the Raman scattered photons 590, a more optimal positioning of the detector 510 may be that shown in FIG. 11, with the detector 510 positioned in substantially the same axis as the direction of the laser radiation. It should be understood that the detector 510 may include a monochromator 530 or another suitable device for determining the wavelength of the Raman scattered photons 590 and a device such as, for example, a photomultiplier for determining the intensity of the emitted Raman scattered photons 590. A filter or a plurality of filters 540 may be employed, either included with the structure of the detector 510 or as a separate unit, that is configured to filter 540 the wavelength of the excitation radiation 190, thus, allowing only the Raman scattered photons 590 to be received by the detector 510.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. An irradiation device, comprising:
   an optical waveguide comprising an active region disposed therein, wherein the optical waveguide is configured for generating an amplified radiation;
   an optical modulator disposed adjacent to at least one surface of the active region and configured for operation in a variably transmissive state;
   an exposure region disposed adjacent to the optical modulator and configured to be illuminated with a variable intensity of the amplified radiation transmitted through the optical modulator when the optical modulator is configured in the variably transmissive state; and
   an area configured to receive a medium of interest within the exposure region and configured to receive an excitation radiation of the amplified radiation.

2. The irradiation device of claim 1, wherein the exposure region is substantially obscured from the amplified radiation when the variably transmissive state of the optical modulator is configured as substantially non-transmissive.

3. The irradiation device of claim 1, wherein the optical waveguide is optically pumped by an incident pump radiation impinging on the optical waveguide.

4. The device of claim 1, wherein the active region includes at least one quantum well.

5. The device of claim 1, wherein the active region comprises a two-dimensional photonic crystal material including at least one defect forming a high-Q cavity therein.

6. The device of claim 1, wherein the optical waveguide comprises a first Bragg reflector, a second Bragg reflector in a plane substantially parallel to the first Bragg reflector, and the active region disposed between the first Bragg reflector and the second Bragg reflector.

7. The device of claim 6, wherein the active region includes at least one quantum well.

8. The device of claim 6, wherein the active region comprises a two-dimensional photonic crystal material including at least one defect forming a high-Q cavity therein.

9. The device of claim 6, wherein the optical modulator is disposed in the first Bragg reflector.

10. The device of claim 6, wherein the optical modulator is disposed in the second Bragg reflector.

11. The irradiation device of claim 6, wherein the first Bragg reflector comprises a P-doped material, the second Bragg reflector comprises an N-doped material and the optical waveguide is electrically pumped by an electrical signal operably coupled between the first Bragg reflector and the second Bragg reflector.

12. The irradiation device of claim 6, wherein the first Bragg reflector comprises an N-doped material, the second Bragg reflector comprises a P-doped material and the optical waveguide is electrically pumped by an electrical signal operably coupled between the first Bragg reflector and the second Bragg reflector.

13. The device of claim 1, wherein the optical modulator is disposed in the active region.

14. The device of claim 1, wherein the optical modulator further comprises a modulation signal, and wherein the optical modulator operates in the variably transmissive state with a transmission rate proportional to a magnitude of the modulation signal.

15. The device of claim 14, wherein the modulation signal comprises an electrical signal.

16. The device of claim 1, wherein the medium of interest comprises a photo-luminescent compound disposed within the exposure region and configured to emit a selected light wavelength when exposed to an excitation radiation of the amplified radiation.

17. The device of claim 16, wherein the photo-luminescent compound is selected from the group consisting of a compound that emits substantially red light, a compound that emits substantially green light, and a compound that emits substantially blue light.

18. The device of claim 16, wherein the optical modulator further comprises a modulation signal, wherein the optical modulator operates in the variably transmissive state with a transmission rate proportional to a magnitude of the modulation signal.

19. The device of claim 18, wherein the photo-luminescent compound emits a variable intensity of the selected light wavelength proportional to the transmission rate of the optical modulator.

20. The device of claim 1, further comprising a SERS-active structure disposed within the exposure region and configured to accept an analyte thereon, wherein the SERS-active structure and the analyte are configured to emit a Raman scattered radiation when exposed to the amplified radiation.

21. An irradiation array, comprising a plurality of irradiation devices formed on a substrate, wherein each irradiation device of the plurality of irradiation devices comprises:
   an optical modulator configured for operation in a variably transmissive state;
   an active region formed in an optical waveguide, wherein the optical modulator is adjacent to at least one surface of the active region and is configured for generating an amplified radiation derived from an incident pump radiation impinging on the optical waveguide when the variably transmissive state of the optical modulator is configured as substantially non-transmissive;
   an exposure region adjacent to the optical modulator and configured to be illuminated by the amplified radiation when the optical modulator is configured in the variably transmissive state; and
   an area configured to receive a medium of interest within the exposure region and configured to receive an excitation radiation of the amplified radiation.

22. The irradiation array of claim 21, wherein the active region of each of the plurality of irradiation devices includes at least one quantum well.

23. The irradiation array of claim 21, wherein the active region of each of the plurality of irradiation devices comprises a two-dimensional photonic crystal material disposed in the optical waveguide of that device, the two-dimensional photonic crystal material including at least one defect forming a high-Q cavity therein.

24. The irradiation array of claim 21, wherein the optical waveguide of each of the plurality of irradiation devices comprises a first Bragg reflector, a second Bragg reflector in a plane substantially parallel to the first Bragg reflector, and the active region disposed between the first Bragg reflector and the second Bragg reflector.

25. The irradiation array of claim 24, wherein the active region of each of the plurality of irradiation devices includes at least one quantum well.

26. The irradiation array of claim 24, wherein the active region of each of the plurality of irradiation devices comprises a two-dimensional photonic crystal material disposed in the optical waveguide, the two-dimensional photonic crystal material including at least one defect forming a high-Q cavity therein.

27. The irradiation array of claim 24, wherein the optical modulator of each of the plurality of irradiation devices is disposed in the first Bragg reflector of that irradiation device.

28. The irradiation array of claim 24, wherein the optical modulator of each of the plurality of irradiation devices is disposed in the second Bragg reflector of that irradiation device.

29. The irradiation array of claim 21, wherein the optical modulator of each of the plurality of irradiation devices is disposed in the active region of that irradiation device.

30. The irradiation array of claim 21, wherein the optical modulator of each of the plurality of irradiation devices further comprises a modulation signal, wherein the optical modulator of each of the plurality of irradiation devices operates in the variably transmissive state with a transmission rate proportional to a magnitude of the modulation signal for that optical modulator.

31. The irradiation array of claim 30, wherein the modulation signal of each of the plurality of irradiation devices comprises an electrical signal.

32. The irradiation array of claim 21, wherein the medium of interest comprises a photo-luminescent compound disposed within the exposure region of each of the plurality of irradiation devices, and configured to emit a selected light wavelength when exposed to the amplified radiation.

33. The irradiation array of claim 32, wherein the photo-luminescent compound of each of the plurality of irradiation devices emits a variable intensity of the selected light wavelength proportional to the transmission rate of the optical modulator for that irradiation device.

34. The irradiation array of claim 21, wherein;
   a first portion of the plurality of irradiation devices further comprises a first photo-luminescent compound, disposed within the exposure region of the first portion of the plurality of irradiation devices, and configured to emit a first light wavelength when exposed to the amplified radiation;

a second portion of the plurality of irradiation devices further comprises a second photo-luminescent compound, disposed within the exposure region of the second portion of the plurality of irradiation devices, and configured to emit a second light wavelength when exposed to the amplified radiation; and a third portion of the plurality of irradiation devices further comprises a third photo-luminescent compound, disposed within the exposure region of the third portion of the plurality of irradiation devices, and configured to emit a third light wavelength when exposed to the amplified radiation.

35. The irradiation array of claim 34, wherein the first photo-luminescent compound emits substantially red light, the second photo-luminescent compound emits substantially green light, and the third photo-luminescent compound emits substantially blue light.

36. The irradiation array of claim 21, further comprising a SERS-active structure disposed within the exposure region of at least one of the plurality of irradiation devices and configured to accept an analyte thereon, wherein the SERS-active structure and the analyte are configured to emit a Raman scattered radiation when exposed to the amplified radiation from the at least one of the plurality of irradiation devices.

37. An amplification and irradiation method, comprising:
generating an amplified radiation in an active region of an optical waveguide;
transmitting a variable intensity of the amplified radiation through an optical modulator disposed adjacent to at least one surface of the active region by configuring the optical modulator in a variably transmissive state;
illuminating an exposure region disposed adjacent to the optical modulator with the variable intensity of the amplified radiation; and
exposing a photo-luminescent compound to the amplified radiation to emit a selected light wavelength.

38. The method of claim 37, wherein generating the amplified radiation further comprises stimulating the optical waveguide with an electrical pump.

39. The method of claim 37, wherein generating the amplified radiation further comprises illuminating the optical waveguide with an incident pump radiation.

40. The method of claim 39, wherein generating the amplified radiation further comprises generating additional amplification by way of a two-dimensional photonic crystal material including a defect forming a high-Q cavity therein.

41. The method of claim 37, further comprising varying an intensity of the amplified radiation in proportion to a varying transmissivity of the optical modulator.

42. The method of claim 41, further comprising varying the transmissivity of the optical modulator in proportion to a modulation signal controlling the varying transmissivity of the optical modulator.

43. The method of claim 37, further comprising varying an intensity of the amplified radiation in proportion to a varying transmissivity of the optical modulator.

44. The method of claim 43, further comprising varying an intensity of the selected light wavelength emission from the photo-luminescent compound in proportion to the intensity of the amplified radiation.

45. The method of claim 37, wherein the photo-luminescent compound is selected from the group consisting of a compound that emits substantially red light, a compound that emits substantially green light, and a compound that emits substantially blue light.

46. The method of claim 37, further comprising causing emission of a Raman scattered radiation when the amplified radiation illuminates a SERS-active structure disposed within the exposure region and an analyte disposed on the SERS-active structure.

* * * * *

UNITED STATES PATENT AND TRADEMARK OFFICE
CERTIFICATE OF CORRECTION

PATENT NO. : 7,609,376 B2 Page 1 of 1
APPLICATION NO. : 10/968427
DATED : October 27, 2009
INVENTOR(S) : Shih-Yuan Wang et al.

It is certified that error appears in the above-identified patent and that said Letters Patent is hereby corrected as shown below:

On the Title page, Item (75), Inventors, in column 1, line 2, delete "Mountain View," and insert -- Sacramento, --, therefor.

Signed and Sealed this

Twenty-seventh Day of April, 2010

David J. Kappos
*Director of the United States Patent and Trademark Office*